(12) United States Patent
Madison

(10) Patent No.: US 6,706,504 B1
(45) Date of Patent: Mar. 16, 2004

(54) TISSUE TYPE PLASMINOGEN ACTIVATOR (T-PA) VARIANTS: COMPOSITIONS AND METHODS OF USE

(75) Inventor: Edwin L. Madison, Del Mar, CA (US)

(73) Assignee: The Scripps Research Institute, La Jolla, CA (US)

(*) Notice: Subject to any disclaimer, the term of this patent is extended or adjusted under 35 U.S.C. 154(b) by 0 days.

(21) Appl. No.: 09/600,985

(22) PCT Filed: Nov. 12, 1997

(86) PCT No.: PCT/US97/20226

§ 371 (c)(1),
(2), (4) Date: Nov. 13, 2000

(87) PCT Pub. No.: WO98/21320

PCT Pub. Date: May 22, 1998

Related U.S. Application Data

(60) Provisional application No. 60/030,655, filed on Nov. 12, 1996.

(51) Int. Cl.[7] .................................................. C12N 9/00
(52) U.S. Cl. ........................................................ 435/183
(58) Field of Search ........................... 424/94.64, 94.63; 435/212, 435

(56) References Cited

U.S. PATENT DOCUMENTS

| | | | | |
|---|---|---|---|---|
| 5,246,850 A | * | 9/1993 | Bennett et al. | 435/212 |
| 5,520,913 A | * | 5/1996 | Anderson et al. | 424/94.63 |
| 5,525,477 A | * | 6/1996 | Hassouna | 435/13 |
| 5,616,486 A | | 4/1997 | Anderson et al. | |

FOREIGN PATENT DOCUMENTS

| | | |
|---|---|---|
| EP | 0 199 574 | 10/1986 |
| EP | 0 201 153 | 11/1986 |
| EP | 0 225 286 | 6/1987 |
| EP | 0 231 624 | 8/1987 |
| EP | 0 233 013 | 8/1987 |
| EP | 0 238 304 | 9/1987 |
| EP | 0 240 334 | 10/1987 |
| EP | 0 241 209 | 10/1987 |
| EP | 0 290 118 | 11/1988 |
| EP | 0 292 009 | 11/1988 |
| EP | 0 293 934 | 12/1988 |
| EP | 0 293 936 | 12/1988 |
| EP | 0 297 066 | 12/1988 |
| EP | 0 299 706 | 1/1989 |
| EP | 0 351 246 | 1/1990 |
| WO | WO 87/04722 | 8/1987 |
| WO | WO 88/05081 | 7/1988 |
| WO | WO 88/10119 | 12/1988 |
| WO | WO 89/00191 | 1/1989 |
| WO | WO 90/02798 | 3/1990 |

OTHER PUBLICATIONS

Tate KM, Higgins DL, Holmes WE, Winkler ME, Heyneker HL, Vehar GA. Functional role of proteolytic cleavage at arginine–275 of human tissue plasminogen activator as assessed by site–directed mutagensis. Biochemistry. Jan. 27, 1987;26(2):338–43.*

Petersen LC, Boel E, Johannessen M. Foster D. Quenching of the amidolytic activity of one–chain tissue–type plasminogen activator by mutation of lysine–416. Biochemistry. Apr. 10, 1990;29(14):3451–7.*

Lamba D, Bauer M, Huber R, Fischer S, Rudolph R, Kohnert U, Bode W. The 2.3 A crystal structure of the catalytic domain of recombinant two–chain human tissue–type plasminogen activator. J Mol Biol. Apr. 26, 1996;258(1):117–35.*

Strandberg L, Madison EL. Variants of tissue–type plasminogen activator with substantially enhanced response and selectivity toward fibrin co–factors. J Biol Chem. Oct. 6, 1995;270(40):23444–9.*

Petersen, et al., Quenching of the amidolytic activity of one–chain tissue–type plasminogen activator by mutation of lysine–416, 1990, *Biochemistry*, 29(14):3451–3457.

Tachias, et al., Variants of tissue–type plasminogen activator which display substantially enhanced stimulation by fibrin, 1995, *J. Biol. Chem.*, 270(31):18319–18322.

Krause, et al., Properties of molecular variants of tissue–type plasminogen activator, 1989, *Arzneim.–Forsch.*, 39:632–637.

van Zonneveld, et al., Mapping of epitopes on human tissue–type plasminogen activator with recombinant deletion mutant proteins, 1987, *Thrombosis & Haemostasis*, 57(1):82–86.

Browne, et al., A tissue–type plasminogen activator mutant with prolonged clearance in vivo. Effect of removal of the growth factor domain, 1988, *J. Biol. Chem.*, 263:1599–1602.

Madison, et al., Serpin resistant mutants of human tissue–type plasminogen activator, 1989, *Nature*, 339:721–724.

Higgins, et al., The effect of the one–chain to two–chain conversion in tissue plasminogen activator: Characterization of mutations at position 275, 1990, *Thrombosis Res.*, 57:527–539.

\* cited by examiner

*Primary Examiner*—Karen Cochrane Carlson
*Assistant Examiner*—Sheridan Snedden
(74) *Attorney, Agent, or Firm*—Thomas Fitting

(57) ABSTRACT

Variants of tissue plasminogen factor exhibit significantly enhanced fibrin stimulation, dramatically increased discrimination among fibrin co-factors, marked resistance to inhibition by PAI-1, and substantially increased zymogenicity, a combination of properties that enhance the therapeutic utility of the enzyme.

22 Claims, 4 Drawing Sheets

GTTCTGAGCACAGGGCTGGAGAGAAAACCTCTGCGAGGAAAGGGAAGGAGCAAGCCGTGA

ATTTAAGGGACGCTGTGAAGCAATC

```
                                  -35                      -30
                                  met  asp  ala  met  lys  arg  gly  leu
                                  ATG  GAT  GCA  ATG  AAG  AGA  GGG  CTC -20
cys  cys  val  leu  leu  leu  cys  gly  ala  val  phe  val  ser  pro  ser
TGC  TGT  GTG  CTG  CTG  CTG  TGT  GGA  GCA  GTC  TTC  GTT  TCG  CCC  AGC -10                                             1
gln  glu  ile  his  ala  arg  phe  arg  arg  gly  ala  arg  SER  TYR  GLN
CAG  GAA  ATC  CAT  GCC  CGA  TTC  AGA  AGA  GGA  GCC  AGA  TCT  TAC  CAA 10
VAL  ILE  CYS  ARG  ASP  GLU  LYS  THR  GLN  MET  ILE  TYR  GLN  GLN  HIS
GTG  ATC  TGC  AGA  GAT  GAA  AAA  ACG  CAG  ATG  ATA  TAC  CAG  CAA  CAT 20                                              30
GLN  SER  TRP  LEU  ARG  PRO  VAL  LEU  ARG  SER  ASN  ARG  VAL  GLU  TYR
CAG  TCA  TGG  CTG  CGC  CCT  GTG  CTC  AGA  AGC  AAC  CGG  GTG  GAA  TAT 40
CYS  TRP  CYS  ASN  SER  GLY  ARG  ALA  GLN  CYS  HIS  SER  VAL  PRO  VAL
TGC  TGG  TGC  AAC  AGT  GGC  AGG  GCA  CAG  TGC  CAC  TCA  GTG  CCT  GTC 50                                              60
LYS  SER  CYS  SER  GLU  PRO  ARG  CYS  PHE  ASN  GLY  GLY  THR  CYS  GLN
AAA  AGT  TGC  AGC  GAG  CCA  AGG  TGT  TTC  AAC  GGG  GGC  ACC  TGC  CAG 70
GLN  ALA  LEU  TYR  PHE  SER  ASP  PHE  VAL  CYS  GLN  CYS  PRO  GLU  GLY
CAG  GCC  CTG  TAC  TTC  TCA  GAT  TTC  GTG  TGC  CAG  TGC  CCC  GAA  GGA 80                                              90
PHE  ALA  GLY  LYS  CYS  CYS  GLU  ILE  ASP  THR  ARG  ALA  THR  CYS  TYR
TTT  GCT  GGG  AAG  TGC  TGT  GAA  ATA  GAT  ACC  AGG  GCC  ACG  TGC  TAC 100
GLU  ASP  GLN  GLY  ILE  SER  TYR  ARG  GLY  THR  TRP  SER  THR  ALA  GLU
GAG  GAC  CAG  GGC  ATC  AGC  TAC  AGG  GGC  ACG  TGG  AGC  ACA  GCG  GAG 110                                             120
SER  GLY  ALA  GLU  CYS  THR  ASN  TRP  ASN  SER  SER  ALA  LEU  ALA  GLN
AGT  GGC  GCC  GAG  TGC  ACC  AAC  TGG  AAC  AGC  AGC  GCG  TTG  GCC  CAG 130
LYS  PRO  TYR  SER  GLY  ARG  ARG  PRO  ASP  ALA  ILE  ARG  LEU  GLY  LEU
AAG  CCC  TAC  AGC  GGG  CGG  AGG  CCA  GAC  GCC  ATC  AGG  CTG  GGC  CTG 140                                             150
GLY  ASN  HIS  ASN  TYR  CYS  ARG  ASN  PRO  ASP  ARG  ASP  SER  LYS  PRO
GGG  AAC  CAC  AAC  TAC  TGC  AGA  AAC  CCA  GAT  CGA  GAC  TCA  AAG  CCC 160
TRP  CYS  TYR  VAL  PHE  LYS  ALA  GLY  LYS  TYR  SER  SER  GLU  PHE  CYS
TGG  TGC  TAC  GTC  TTT  AAG  GCG  GGG  AAG  TAC  AGC  TCA  GAG  TTC  TGC 170                                             180
SER  THR  PRO  ALA  CYS  SER  GLU  GLY  ASN  SER  ASP  CYS  TYR  PHE  GLY
AGC  ACC  CCT  GCC  TGC  TCT  GAG  GGA  AAC  AGT  GAC  TGC  TAC  TTT  GGG
```

Fig. 1A.

```
                              190
ASN GLY SER ALA TYR ARG GLY THR HIS SER LEU THR GLU SER GLY
AAT GGG TCA GCC TAC CGT GGC ACG CAC AGC CTC ACC GAG TCG GGT 200                                   210
ALA SER CYS LEU PRO TRP ASN SER MET ILE LEU ILE GLY LYS VAL
GCC TCC TGC CTC CCG TGG AAT TCC ATG ATC CTG ATA GGC AAG GTT

220
TYR THR ALA GLN ASN PRO SER ALA GLN ALA LEU GLY LEU GLY LYS
TAC ACA GCA CAG AAC CCC AGT GCC CAG GCA CTG GGC CTG GGC AAA 230                                   240
HIS ASN TYR CYS ARG ASN PRO ASP GLY ASP ALA LYS PRO TRP CYS
CAT AAT TAC TGC CGG AAT CCT GAT GGG GAT GCC AAG CCC TGG TGC

250
HIS VAL LEU LYS ASN ARG ARG LEU THR TRP GLU TYR CYS ASP VAL
CAC GTG CTG AAG AAC CGC AGG CTG ACG TGG GAG TAC TGT GAT GTG 260                                   270
PRO SER CYS SER THR CYS GLY LEU ARG GLN TYR SER GLN PRO GLN
CCC TCC TGC TCC ACC TGC GGC CTG AGA CAG TAC AGC CAG CCT CAG

280
PHE ARG ILE LYS GLY GLY LEU PHE ALA ASP ILE ALA SER HIS PRO
TTT CGC ATC AAA GGA GGG CTC TTC GCC GAC ATC GCC TCC CAC CCC 290                                   300
TRP GLN ALA ALA ILE PHE ALA LYS HIS ARG ARG SER PRO GLY GLU
TGG CAG GCT GCC ATC TTT GCC AAG CAC AGG AGG TCG CCC GGA GAG

310
ARG PHE LEU CYS GLY GLY ILE LEU ILE SER SER CYS TRP ILE LEU
CGG TTC CTG TGC GGG GGC ATA CTC ATC AGC TCC TGC TGG ATT CTC 320                                   330
SER ALA ALA HIS CYS PHE GLN GLU ARG PHE PRO PRO HIS HIS LEU
TCT GCC GCC CAC TGC TTC CAG GAG AGG TTT CCG CCC CAC CAC CTG

340
THR VAL ILE LEU GLY ARG THR TYR ARG VAL VAL PRO GLY GLU GLU
ACG GTG ATC TTG GGC AGA ACA TAC CGG GTG GTC CCT GGC GAG GAG 350                                   360
GLU GLN LYS PHE GLU VAL GLU LYS TYR ILE VAL HIS LYS GLU PHE
GAG CAG AAA TTT GAA GTC GAA AAA TAC ATT GTC CAT AAG GAA TTC

370
ASP ASP ASP THR TYR ASP ASN ASP ILE ALA LEU LEU GLN LEU LYS
GAT GAT GAC ACT TAC GAC AAT GAC ATT GCG CTG CTG CAG CTG AAA 380                                   390
SER ASP SER SER ARG CYS ALA GLN GLU SER SER VAL VAL ARG THR
TCG GAT TCG TCC CGC TGT GCC CAG GAG AGC AGC GTG GTC CGC ACT

400
VAL CYS LEU PRO PRO ALA ASP LEU GLN LEU PRO ASP TRP THR GLU
GTG TGC CTT CCC CCG GCG GAC CTG CAG CTG CCG GAC TGG ACG GAG 410                                   420
CYS GLU LEU SER GLY TYR GLY LYS HIS GLU ALA LEU SER PRO PHE
TGT GAG CTC TCC GGC TAC GGC AAG CAT GAG GCC TTG TCT CCT TTC
```

Fig. 1B.

```
                        430
TYR SER GLU ARG LEU LYS GLU ALA HIS VAL ARG LEU TYR PRO SER
TAT TCG GAG CGG CTG AAG GAG GCT CAT GTC AGA CTG TAC CCA TCC 440                                         450
SER ARG CYS THR SER GLN HIS LEU LEU ASN ARG THR VAL THR ASP
AGC CGC TGC ACA TCA CAA CAT TTA CTT AAC AGA ACA GTC ACC GAC

460
ASN MET LEU CYS ALA GLY ASP THR ARG SER GLY GLY PRO GLN ALA
AAC ATG CTG TGT GCT GGA GAC ACT CGG AGC GGC GGG CCC CAG GCA 470                                         480
ASN LEU HIS ASP ALA CYS GLN GLY ASP SER GLY GLY PRO LEU VAL
AAC TTG CAC GAC GCC TGC CAG GGC GAT TCG GGA GGC CCC CTG GTG

490
CYS LEU ASN ASP GLY ARG MET THR LEU VAL GLY ILE ILE SER TRP
TGT CTG AAC GAT GGC CGC ATG ACT TTG GTG GGC ATC ATC AGC TGG 500                                         510
GLY LEU GLY CYS GLY GLN LYS ASP VAL PRO GLY VAL TYR THR LYS
GGC CTG GGC TGT GGA CAG AAG GAT GTC CCG GGT GTG TAC ACC AAG 520                     527
VAL THR ASN TYR LEU ASP TRP ILE ARG ASP ASN MET ARG PRO OP
GTT ACC AAC TAC CTA GAC TGG ATT CGT GAC AAC ATG CGA CCG TGA
```

CCAGGAACACCCGACTCCTCAAAAGCAAATGAGATCCCGCCTCTTCTTCTTCAGAAGACA

CTGCAAAGGCGCAGTGCTTCTCTACAGACTTCTCCAGACCCACCACACCGCAGAAGCGGG

ACGAGACCCTACAGGAGAGGGAAGAGTGCATTTTCCCAGATACTTCCCATTTTGGAAGT

TTTCAGGACTTGGTCTGATTTCAGGATACTCTGTCAGATGGGAAGACATGAATGCACACT

AGCCTCTCCAGGAATGCCTCCTCCCTGGGCAGAAAGTGGCCATGCCACCCTGTTTTCAGCTA

AAGCCCAACCTCCTGACCTGTCACCGTGAGCAGCTTTGGAAACAGGACCACAAAAATGAA

AGCATGTCTCAATAGTAAAAGATAACAAGATCTTTCAGGAAAGACGGATTGCATTAGAA

ATAGACAGTATATTTATAGTCACAAGAGCCCAGCAGGGCCTCAAAGTTGGGGCAGGCTGGC

TGGCCCGTCATGTTCCTCAAAAGCACCCTTGACGTCAAGTCTCCTTCCCCTTTCCCCACT

CCCTGGCTCTCAGAAGGTATTCCTTTTGTGTACAGTGTGTAAAGTGTAAATCCTTTTTCT

TTATAAACTTTAGAGTAGCATGAGAGAATTGTATCATTTGAACAACTAGGCTTCAGCATA

TTTATAGCAATCCATGTTAGTTTTTACTTTCTGTTGCCACAACCCTGTTTTATACTGTA

CTTAATAAATTCAGATATATTTTTCACAGTTTTTCCAAAAAAAAAAAAAAA

Fig. 1C.

TISSUE TYPE PLASMINOGEN ACTIVATOR (T-PA) VARIANTS: COMPOSITIONS AND METHODS OF USE

REFERENCE TO RELATED APPLICATION

This application claims the of PCT/US97/20226, filed Nov. 12, 1997, which claims the benefit of U.S. Provisional Application Ser. No. 60/030,655, filed Nov. 12, 1996, which is incorporated by reference.

This invention was made with government support under Contract Nos. R01 52475 and P01 HL 31950 by the National Institutes of Health. The government has certain rights in the invention.

GOVERNMENTAL RIGHTS

This invention was made with governmental support from the United States Government, National Institutes of Health, Grants HL52475 and HL31950; the United States Government has certain rights in the invention.

The invention comprises protein single chain variants of tissue type plasminogen activator, also referred to as t-PA as well as nucleic acids encoding such protein single chain variants of tissue type plasminogen activator. The t-PA protein variants have higher zymogenicity than the wild-type single chain t-PA form. Methods of making and using the t-PA variant compositions are also described.

BACKGROUND

Tissue-type plasminogen activator (t-PA) is a serine protease that plays a critical role in the process of fibrinolysis, the dissolution of clots, by activating plasminogen to the protease plasmin. t-PA has been fully identified and characterized by underlying DNA sequence and deduced amino acid sequence. See Pennica et al., *Nature*, 301: 214 (1983) and U.S. Pat. No. 4,853,330, issued Aug. 1, 1989, the teachings of both of which are incorporated by reference. The nucleotide sequence and deduced primary amino acid sequence of human t-PA is depicted in FIG. 1A, FIG. 1B and FIG. 1C.

The group of amino acid residues from −35 to −1 preceding the sequence of the mature t-PA is the "pro" sequence. The mature t-PA molecule (amino acid residues 1–527) contains five domains that have been defined with reference to homologous or otherwise similar structures identified in various other proteins such as trypsin, chymotrypsin, plasminogen, prothrombin, fibronectin, and epidermal growth factor (EGF). These domains have been designated, starting at the N-terminus of the amino acid sequence of mature t-PA, as 1) the finger region (F) that has variously been defined as including amino acid residues 1 to about 44, 2) the growth factor region (G) that has been variously defined as stretching from about amino acid residues 45 to 91 (based upon its homology with EGF), 3) kringle one (K1) that has been defined as stretching from about amino acid residue 92 to about amino acid residue 173, 4) kringle two (K2) that has been defined as stretching from about amino acid residue 180 to about amino acid residue 261, and 5) the so-called serine protease domain (P) that generally has been defined as stretching from about amino acid residue 264 to the C-terminal end of the molecule at amino acid residue 527. These domains, which are situated generally adjacent to one another, or are separated by short "linker" regions, account for the entire amino acid sequence of from 1 to 527 amino acid residues of the mature form of t-PA.

Each domain has been described variously as contributing certain specific biologically significant properties. The finger domain has been characterized as containing a sequence of at least major importance for high binding affinity to fibrin. (This activity is thought important for the high specificity that t-PA displays with respect to clot lysis at the locus of a fibrin-rich thrombus.) The growth factor-like region likewise has been associated with cell surface binding activity. The kringle 2 region also has been strongly associated with fibrin binding and with the ability of fibrin to stimulate the activity of t-PA. The serine protease domain is responsible for the enzymatic cleavage of plasminogen to produce plasmin.

t-PA is unusual among proteases in the level of the enzymatic activity of its precursor. In general, proteases are synthesized as zymogens, inactive precursors that must either be proteolytically processed or bind to a specific co-factor to develop substantial catalytic activity. The increase in catalytic efficiency after zymogen activation, or zymogenicity, is dramatic in almost all cases, although varying widely among individual members of the chymotrypsin family. For example, strong zymogens, i.e., those having high zymogenicity, such as trypsinogen, chymotrypsinogen, or plasminogen are almost completely inactive, with measured zymogenicities of $10^4$ to $10^6$ (Robinson, N. C., Neurath, H., and Walsh, K. A. (1973) *Biochemistry* 12, 420–426; Gertler, A., Walsh, K. A., and Neurath, H. (1974) *Biochemistry* 13, 1302–1310). Other serine proteases exhibit intermediate zymogenicity. For example, the enzymatic activity of Factor XIIa is 4000-fold greater than that of its corresponding zymogen, Factor XII (Silverberg, M., and Kaplan, A. P. (1982) Blood 60, 64), and the catalytic efficiency of urokinase is 250-fold greater than that of pro-urokinase (Lijnen, H. R., Van Hoef, B., Nelles, L., and Collen, D. (1990) *J. Biol. Chem.* 265, 5232–5236). By contrast, the catalytic activities of single and two chain t-PA vary by a factor of only 5–10.

The zymogenicity, expressed as the ratio of the activity of the mature cleaved two-chain enzyme to that of the single chain precursor form, is only 5–10 for wild-type t-PA, in contrast to other precursors of other proteases that have little or no catalytic activity. Thus, the single chain form of wild-type t-PA is not a true zymogen.

There have been many attempts to improve the usefulness of t-PA by genetic engineering. These efforts have been only partially successful. The state of the art has been reviewed by Krause, J., & Tanswell, P. *Arzneim.-Forsch*. 39: 632–637 (1989) and in U.S. Pat. No. 5,616,486, the teachings of both of which are incorporated by reference.

Despite the profound advantages associated with natural t-PA as a clot-dissolving agent, it is not believed that the natural protein necessarily represents the optimal t-PA agent under all circumstances. Therefore, several variants have been proposed or devised to enhance specific properties of t-PA. Certain of those variants address disadvantages associated with the use of natural t-PA in situations where an agent with a longer half-life or slower clearance rate would be preferred, e.g., in the treatment of deep-vein thrombosis and following reperfusion of an infarct victim, or where a single-chain agent is preferred.

For example, removal of a substantial portion or all of the finger domain results in a molecule with substantially diminished fibrin binding characteristics, albeit in return there is a decrease in the overall rate of clearance of the resultant entity—See WO 89/00197 published Jan. 12, 1989.

Variants are described in EPO Pat. Publ. No. 199,574 that have amino acid substitutions at the proteolytic cleavage sites at positions 275, 276, and 277. These variants, characterized preferentially as t-PA variants having an amino acid other than arginine at position 275, are referred to as protease-resistant one-chain t-PA variants in that, unlike natural t-PA, which can exist in either a one-chain or two-chain form, they are resistant to protease cleavage at position 275 and are therefore not converted metabolically in vivo into a two-chain form. This form is thought to have certain advantages biologically and commercially, in that it is more stable while the fibrin binding and fibrin stimulation are increased relative to two-chain t-PA. Furthermore, plasminogen activators are described that comprise one domain capable of interacting with fibrin and the protease domain of urokinase, with one embodiment being urokinase altered to make it less susceptible to forming two-chain urokinase. See WO 88/05081 published Jul. 14, 1988.

For further patent literature regarding modification of the protease cleavage site of t-PA, see, for example, EPO Pat. Nos. 241,209; EP 201,153 published Nov. 12, 1986; EP 233,013 published Aug. 19, 1987; EP 292,009 published Nov. 23, 1988, EP 293,936 published Dec. 7, 1988; and EP 293,934 published Dec. 7, 1988; and WO 88/10119.

Glycosylation mutants at positions 117–119, 184–186, and 448–450 exhibited higher specific activity as the mole percent carbohydrate was reduced. See EPO Pub. No. 227, 462 published Jul. 1, 1987. This patent application additionally discloses using an assay of fibrin/fibrin degradation products and teaches that one may also modify the t-PA molecule at positions 272–280 or delete up to 25 amino acids from the C-terminus. Further, the t-PA mutants with Asn 119, Ala 186 and Asn 450, which have the N-glycosylation sites selectively removed by DNA modification but contain residual O-linked carbohydrate, were found to be about two-fold as potent as melanoma t-PA in an in vitro lysis assay. See EPO Publ. No. 225,286 published Jun. 10, 1987.

Replacement of the amino acid at position 449 of t-PA with any amino acid except arginine to modify the glycosylation site, as well as modification of Arg 275 or deletion of the −3 to 91 region, is also taught. See WO 87/04722 published Aug. 13, 1987. An amino acid substitution at position 448 of t-PA is disclosed as desirable to remove glycosylation. See EPO Pub. No. 297,066 published Dec. 28, 1988. The combination of modifications at positions 448–450 and deletion of the N-terminal 1–82 amino acids is disclosed by WO 89/00191 published Jan. 12, 1989. Additionally, urokinase has been modified in the region of Asp 302-Ser 303-Thr 304 to prevent glycosylation. See EPO Pub. No. 299,706 published Jan. 18, 1989.

However, alteration of the glycosylation sites, and in particular that at amino acid 117, seems invariably to result in a molecule having affected solubility characteristics that may result additionally in an altered circulating half-life pattern and/or fibrin binding characteristics. See EPO Pat. Publ. No. 238,304, published Sep. 23, 1987.

When the growth factor domain of t-PA is deleted, the resultant variant is still active and binds to fibrin, as reported by A. J. van Zonneveld et al., *Thrombos. Haemostas.* 54 (1): 4 (1985). Various deletions in the growth factor domain have also been reported in the patent literature. See EPO Publ. No. 241,209 (del-51–87), EPO Publ. No. 241,208 (del-51–87 and del-51–173), PCT 87/04722 (deletion of all or part of the N-terminal 1–91), EPO Publ. No. 231,624 (all of growth factor domain delexed), and EPO Publ. No. 242,830 and Jap. Pat. Appl. Kokai No. 62-269688 (some or all of the growth factor domain deleted).

It has further been shown tat t-PA can be modified both in the region of the first kringle domain and in the growth factor domain, resulting in increased circulatory half-life. See EPO Pat. Publ. No. 241,208 published Oct. 14, 1,987. The region between amino acids 51 and 87, inclusive, can be deleted from t-PA to result in a variant having slower clearance from plasma. Browne et al., *J. Biol. Chem.*, 263; 1599–1602 (1988). Also, t-PA can be modified, without adverse biological effects, in the region of amino acids 67 to 69 of the mature, native t-PA, by deletion of certain amino acid residues or replacement of one or more amino acids with different amino acids. See EPO Pat. Publ. No. 240,334 published Oct. 7, 1987.

A hybrid of t-PA/urokinase using the region of t-PA encompassing amino acids 273–527 is also disclosed. See EPO 290,118 published Nov. 9, 1988. Serpin-resistant mutants of human t-PA with alterations in the protease domain, including de1296-302 t-PA, R304S t-PA, and R304E t-PA, are disclosed in Madison et al., *Nature*, 339: 721–724 (1989). The above list is not an exhaustive review of the numerous variants of t-PA that have been described.

As a result of the catalytic activity of precursor t-PA, despite effective clot lysis at targeted sites, nondesirable proteolysis occurs systemically resulting in the deleterious depletion of circulating fibrinogen, α2-anti-plasmin and plasminogen. What is needed are more zymogenic t-PA variant proteins that provide effective local clot lysis with diminished systemic proteolytic effects.

SUMMARY OF THE INVENTION

The present invention provides single chain variant t-PA proteins having at least two substitutions of basic amino acid residues by neutral or acidic amino acid residues, compared to the wild-type human t-PA, as well as polynucleotides encoding such single chain variant t-PA proteins. The single chain variant t-PA proteins of the present invention have the R275 amino acid residue substituted by an amino acid residue chosen from the group consisting of glycine, serine, threonine, asparagine, tyrosine, glutamine, aspartic acid, and glutamic acid. Preferably the single chain variant t-PA proteins of the present invention have the R275 amino acid residue substituted by an amino acid residue chosen from the group consisting of an aspartic acid residue and a glutamic acid residue, and most preferably by a glutamic acid residue.

The single chain variant t-PA proteins of the present invention have additionally at least one other basic amino acid residue in the serine protease region residue substituted by a non-basic amino acid such that the salt bridge interaction normally found in wildtype single chain t-PA between aspartate 477 and lysine 429 is disrupted. Preferably, basic amino acids are replaced with polar or acidic amino acids, and more preferably, amino acid residues chosen from the group consisting of glycine, serine, threonine, asparagine, tyrosine, glutamine, aspartic acid and glutamic acid.

The salt bridge interaction between aspartate 477 and lysine 429 can be disrupted by a substitution at position 477 or 429, or by an appropriate substitution at a position within the serine protease region that provides an alternative salt bridge interaction partner for at least one of aspartate 477 and lysine 429. In one preferred embodiment, the H417 amino acid residue is substituted by an amino acid residue chosen from the group consisting of glycine, serine, threonine, asparagine, tyrosine, glutamine, aspartic acid, and glutamic acid. More preferably the single chain variant t-PA proteins of the present invention have both the R275 amino acid residue and the H417 amino acid residue substituted by an amino acid residue chosen from the group consisting of an aspartic acid residue and a glutamic acid residue. Two exemplary preferred single chain variant t-PA proteins are the t-PA variants designated as R275E,H417E and R275E, H417D.

In another preferred embodiment, the K429 amino acid residue is substituted by an amino acid residue chosen from the group consisting of glycine, serine, threonine, asparagine, tyrosine, glutamine, aspartic acid, and glutamic acid. More preferably the single chain variant t-PA proteins of the present invention have both the R275 amino acid residue and the K429 amino acid residue substituted by an amino acid residue chosen from the group consisting of glycine, serine, threonine, asparagine, tyrosine, glutamine, aspartic acid, and glutamic acid. One preferred single chain variant t-PA protein is the t-PA variant designated as R275E, K429Y.

The single chain variant t-PA proteins of the present invention exhibit greater zymogenicity, expressed as the ratio of the activity of the mature cleaved two-chain enzyme to that of the single chain precursor form, than that of the wild type single chain t-PA protein. The single chain variant t-PA proteins of the present invention have zymogenicity of at least 10, preferably about 50 to about 200.

The single chain variant t-PA proteins of the present invention exhibit a greater fibrin stimulation factor, expressed as the ratio of the catalytic efficiencies in the presence and absence of fibrin, compared to the wild type single chain t-PA protein. The single chain variant t-PA proteins of the present invention have a fibrin stimulation factor of at least 7,000, preferably about 20,000 to about 50,000.

The single chain variant t-PA proteins of the present invention exhibit a reduced inhibition by plasminogen activator inhibitor 1 (PAI-1) to the wild type single chain t-PA protein. The single chain variant t-PA proteins of the present invention are at least a factor of 5, preferably at least a factor of about 9, most preferably at least a factor of about 200 less inhibited by PAI-1 compared to the wild type single chain t-PA protein.

The single chain variant t-PA proteins of the present invention exhibit a greater fibrin selectivity factor, expressed as the ratio of the catalytic efficiencies in the presence fibrin to that in the presence of fibrinogen, compared to the wild type single chain t-PA protein. Preferred embodiments of the single chain variant t-PA proteins of the present invention have a fibrin selectivity factor of at least 10, preferably at least 50, more preferably at least 100.

BRIEF DESCRIPTION OF THE DRAWINGS

In the drawings,

FIGS. 1A, 1B and 1C show the nucleotide sequence and deduced amino acid sequence of the full-length human t-PA cDNA.

DETAILED DESCRIPTION OF THE PREFERRED EMBODIMENTS

Figure 2:
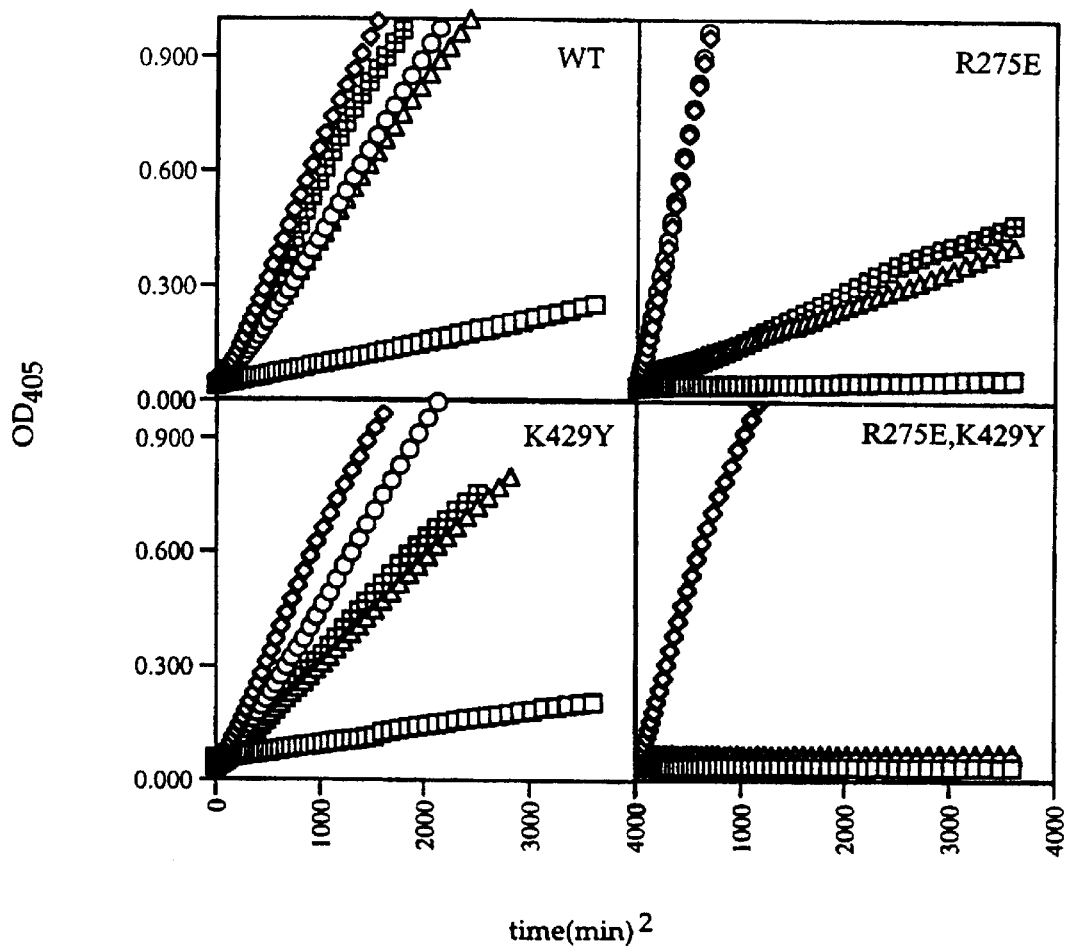
FIG. 2 is a graphical representation of the results of standard chromogenic assays of plasminogen activation in the presence of buffer (open squares), DESAFIB (open diamonds), fibrinogen (open circles), cyanogen bromide fragments of fibrinogen (open triangles) or the stimulatory peptide P368 (hatched squares).

As used herein, "wild-type t-PA" refers to the t-PA protein naturally occurring in humans. While this human t-PA is exemplified by the amino acid sequence depicted in FIGS. 1A, 1B and 1C, the term wild-type t-PA should be understood to encompass naturally occurring allelic variations.

t-PA Variant Compositions

The t-PA variant cDNAs and the corresponding expressed recombinant proteins of this invention are useful compounds that function in the serine protease-mediated control of fibrinolysis as described herein.

The t-PA variant cDNAs of the present invention contain at least one nucleotide substitution to generate a t-PA cDNA that encodes a noncleavable single chain t-PA variant, i.e., not cleavable by plasmin under normal conditions. The nucleotide substitution results in a substitution of a glutamic acid (E) for an arginine (R) at amino acid residue 275 (or position 15 using the chymotrypsin numbering system) in the t-PA precursor that is responsible for creating a noncleavable variant. Positions 15, 144, 156, and 194 of the chymotrypsin numbering system correspond to positions 275, 417, 429, and 477, respectively, in the t-PA numbering system as depicted in FIG. 1.

The variants, which are substitution mutants, are designated by the single letter code of the wild type human t-PA amino acid residue, the position of the residue relative to the amino terminus of the mature human t-PA as depicted in FIG. 1, followed by the single letter code of the amino acid residue substituted for the amino acid residue in mature human t-PA. The substitution of glutamic acid for arginine at position 275 is designated as R275E. Equivalent substitutions generating noncleavable single chain t-PA are known in the art (Higgins, D. L., et al., (1990) *Thrombosis Res.* 57: 527–539).

In addition to the R275E substitution, the variant cDNAs of the present invention further comprise at least one other nucleotide substitution at a separate site to create a t-PA variant having at least two amino acid substitutions. Preferred cDNA variants include at least one nucleotide substitution that results in an amino acid substitution of an amino acid residue chosen from the group consisting of glycine, serine, threonine, asparagine, tyrosine, glutamine, aspartic acid, and glutamic acid for a histidine at amino acid residue position 417. Preferred embodiments are designated R275E,H417D and R275E,H417E. A further cDNA variant comprises at least one nucleotide substitution resulting in the substitution of an amino acid residue chosen from the group consisting of glycine, serine, threonine, asparagine, tyrosine, glutamine, aspartic acid, and glutamic acid for the lysine (K) at amino acid residue position 429. One such preferred embodiment is designated R275E,K429Y.

The variant t-PA cDNAs of the present invention are useful for generating the recombinant expressed variant t-PAs described above. In a further embodiment, the variant t-PA cDNAs have therapeutic uses in gene therapy as described below.

The invention includes embodiments such as expression vectors or plasmids in which the cDNAs for encoding variant t-PAs are operably linked to provide for the expression of recombinant variant t-PAs for use in the methods as described below. One preferred embodiment is the expression of a variant t-PA protein by COS 1 cells comprising pSVT7 expression vector operably linked to a polynucleotide encoding the variant protein. Constitutive and inducible expression vectors are disclosed. In a further embodiment, transiently and stably transfected cells contain cDNA encoding variant t-PAs.

The resultant recombinant expressed t-PA variants described herein are characterized as having one or more of the following structural and functional properties: 1) The t-PA variant is in the form of a noncleavable single chain protein containing an R275E amino acid substitution or equivalents thereof that prevent cleavage by t-PA activating enzymes; 2) The t-PA variant exhibits increased resistance to inhibition by the serpin plasminogen activator inhibitor, type I (PAI-1); 3) The t-PA variants has diminished catalytic activity on substrates, such as plasminogen, in the absence of co-factors, such as fibrin; 4) The t-PA variants exhibit enhanced stimulation by fibrin; 5) The t-PA variants exhibit comparable catalytic activity to substrates, such as plasminogen, in the presence of co-factors, such as fibrin; and 6) In view of the proceeding properties, the t-PA variants thus are effective at local fibrinolysis function without extensive systemic proteolysis thereby negating the depletion of circulating fibrinogen, α2-anti-plasmin and plasminogen, as is seen with wild type human single chain t-PA precursor.

Preferred recombinant expressed t-PA variants thus include R275E,H417D, R275E,H417E and R275E,K429Y, and conservative substitutions thereof. In general, examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. For further discussion of the classifications of amino acids see Lehninger, A. L., Biochemistry, $2^{nd}$ Edition, Worth Publishers, New York, 1975, pp.71–94.

The phrase "conservative substitution" also includes the use of a chemically derivatized residue in place of a non-derivatized residue provided that such protein displays the requisite binding activity. "Chemical derivative" refers to a subject protein having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. D-amino acids may also be included in place of one or more L-amino acids.

In the specific case of the present invention, basic amino acids, i.e., arginine, lysine and histidine are replaced with non-basic amino acids. Preferably basic amino acids are replaced with polar or acidic amino acids, i.e. amino acid residues chosen from the group consisting of glycine, serine, threonine, asparagine, tyrosine, glutamine, aspartic acid and glutamic acid. Conservative substitutions are thus defined, for the purpose of the present invention, as meaning that non-basic amino acids replacing particular basic amino acids in mature wild type human t-PA may be chosen from the group of non-basic amino acids generally, preferably from the group consisting of glycine, serine, threonine, asparagine, tyrosine, glutamine, aspartic acid and glutamic acid, and more preferably from the group consisting of tyrosine, aspartic acid and glutamic acid, For example, the use of aspartic acid instead of glutamic acid to replace an histidine residue is a conservative substitution. Preferred variants are R275E,H417D and R275E,H417E, described in Example 1 and the R275E,K429Y variant, described in Example 2.

The expressed recombinant t-PA variants having at least two amino acid substitutions, e.g., R275E,H417D, R275E, H417E and R275E,K429Y, further exhibit unique properties. R275E and R275E,H417E are activated by both fibrinogen and fibrin while R275E,K429Y is activated primarily by fibrin and is not sensitive to fibrinogen. The latter is also more resistant than the R275E,H417D and R275E,H417E variants to inhibition by PAI-1. These characteristics provide additional advantages in administering the compounds as therapeutic thrombolytic compositions as further described below. In addition, the t-PA variants described herein are useful in diagnostic applications as described below.

Methods of Making and Using t-PA Variant Compositions

Methods of Making

The t-PA variant cDNA and recombinant expressed variant proteins described above are useful in a number of methodological aspects as described in Examples 1 and 2. In particular, the isolated cDNA clones are useful in an expression vector system to produce encoded t-PA variant proteins of this invention. Thus, expression vector systems having a t-PA variant cDNA operably linked therein, including cells containing the expression vectors, are contemplated for generating the recombinant expressed variant proteins of this invention.

Diagnostic Applications

Preferred diagnostic methodological aspects are described herein. In particular, the recombinant expressed t-PA variants of the present invention are useful in diagnostic assays to detect fibrin and fibrin degradation products that have altered activities. The assays are thus indicated in thrombotic conditions. Other diagnostic applications, incuding kits comprising antibodies against the t-PA variants are familiar to one of ordinary skill in the art.

Therapeutic Applications

The t-PA variant cDNAs of the present invention are useful in genetic therapeutic applications for use in ameliorating thrombotic disorders including both acute and chronic conditions. Acute conditions include among others both heart attack and stroke while chronic situations include those of arterial and deep vein thrombosis and restenosis. Preferred therapeutic compositions thus include the cDNA compounds themselves as naked DNA, presented as part of a viral vector delivery system or other vector-based gene expression delivery system, presented in a liposome delivery system and the like.

The recombinant expressed t-PA variant proteins of the present invention are contemplated as thrombolytic therapeutic agents for ameliorating the same conditions outlined above. Based on the individual structural and functional properties of various t-PA variant proteins described above, the selection of the particular t-PA variant is determined by the desired therapeutic outcome. For example, the fibrinogen-mediated activation of endogenous human t-PA is activated by bleeding which then results in a widespread undesired systemic response. Thus, to mediate fibrinolytic processes locally in either an acute or chronic thrombotic condition while simultaneously preventing proteolytic activation systemically, one would therefore use the t-PA variant, namely R275E,K429Y, that is primarily activated by fibrin and not fibrinogen. A composition for use as thrombolytic therapeutic agents generally consists of a physiologically effective amount of the t-PA variant protein in a pharmaceutically suitable excipient. Depending on the mode of administration and the condition to be treated, the thrombolytic therapeutic agents are administered in single or multiple doses. If "bolus" doses are administered, doses of about 0.01 to about 0.6 mg/kg will typically be administered, preferably doses of about 0.05 to about 0.2 mg/kg, with subsequent administrations of about 0.1 to about 0.2 mg/kg to maintain a t-PA blood level of about 3 microgram/ml. One skilled in the art will appreciate that variations in dosage depend on the condition to be treated. In other applications, a composition of variant t-PA in a gel composition is useful in preventing the formation of adhesions.

Other variations and uses of the present invention will be apparent to one skilled in the art.

EXAMPLE 1

Site Directed Mutagenesis and Construction of Expression Vectors Encoding Variants of t-PA Oligonucleoride directed site specific mutagenesis was performed by the method of Zoller and Smith (Zoller, M. I., and Smith, M. (1984) DNA 3, 479–488) as modified by Kunkel (Kunkel, T. A. (1985) Proc. Natl. Acad. Sci. U.S.A 82, 488–492). Mutations were introduced into the 290 bp SacI—SmaI fragment of cDNA encoding t-PA that had been previously subcloned into bacteriophage M13mp18. The mutagenic primers had the following nucleotide sequences:

3: 459–481. See also U.S. Pat. No. 5,550,042, incorporated herein by reference, which describes the construction and use of pSVT7 as well as the deposit with American Type Culture Collection, 12301 Parklawn Dr., Rockville, Md. 20852 of cultures comprising other pSVT7 t-PA constructs. Vectors with ligated cDNA inserts were then introduced into COS 1 cells by electroporation using a Bio Rad Gene Pulser. An aliquot containing 20 µg of cDNA, 100 µg of carrier DNA and approximately $10^7$ COS cells were placed into a 0.4 cm cuvette, and electroporation was performed at 320 V, 960 µFD, and $\Omega=\infty$. Following electroporation, cells were incubated overnight at 37 degrees Celsius in DMEM containing 10% fetal calf serum and 5 mM sodium butyrate. Cells were then washed with serum free medium and incubated in DMEM for 48 hours at 37 degrees Celsius. After the incubation with serum free media, conditioned media were collected. Enzyme concentrations in aliquots of the the collected conditioned media were determined by ELISA.

Kinetic Analysis of Plasminogen Activation Using Indirect Chromogenic Assays Indirect chromogenic assays of t-PA utilized the substrates lys-plasminogen (American Diagnostica, Greenwich, Conn.) and Spectrozyme PL (American Diagnostica) and were performed as previously described (Madison, E. L., Goldsmith, E. J., Gerard, R. D., Gething, M. -J., and Sambrook, J. F. (1989) Nature 339, 721–724; Madison, E. L., Goldsmith, E. J., Gerard, R. D., Gething, M. J., Sambrook, J. F., and Bassel-Duby, R. S. (1990) Proc. Natl. Acad. Sci. U.S.A. 87, 3530–3533; Madison, E. L., Goldsmith, E. J., Gething, M. J., Sambrook, J. F., and Gerard, R. D. (1990) J. Biol. Chem. 265, 21423–21426.). Assays were performed both in the presence and absence of

```
H417D:    5' - CTACGGCAAGGACGAGGCCTTGT - 3'    (SEQ ID NO: 8)

H417E:    5' - CTACGGCAAGGAGGAGGCCTTGT - 3'    (SEQ ID NO: 9)
```

Following mutagenesis, ssDNA corresponding to the entire 290 bp SacI—SmaI fragment was fully sequenced to assure the presence of the desired mutation and the absence of any additional mutations. The sequence corresponding to the 290 bp SacI—SmaI fragment of the H417D mutation is shown in SEQ ID NO: 5; the corresponding sequence of the H417E mutation is shown in SEQ ID NO: 6. Replicative form (RF) DNA was prepared for appropriate phage, and the mutated 290 bp SacI—SmaI fragments were recovered after digestion of RF DNA with SacI and SmaI and electrophoresis of the digestion products on an agarose gel. The isolated, mutated SacI—SmaI fragments were used to replace the corresponding fragment in full length cDNAs encoding wild type human t-PA or t-PA/R275E to yield new, full length cDNAs encoding t-PA/H417D; t-PA/H417E; t-PA/R275E, H417D (SEQ ID NO: 1); and t-PA/R275E,H417E (SEQ ID NO: 2).

Expression of Enzymes by Transient Transfection of COS Cells cDNAs encoding t-PA; t-PA/R275E; t-PA/H417D; t-PA/H417E; t-PA/R275E,H417D; and t-PA/R275E were ligated into the transient expression vector pSVT7 which is described in Madison, E. L., et al. (1989) Nature 339, 721–724; Bird, P. M., et al., (1987) J. Cell Biol. 105: 2905–2914; and Sambrook, J., et al., (1986) Mol. Biol. Med.

the co-factor DESAFIB (American Diagnostica). The concentration of lys-plasminogen was varied from 0.0125–0.2 µM in the presence of DESAFIB and from 0.9–15 µM in the absence of the co-factor.

Kinetic Analysis of t-PA Activity Using a Small, Synthetic Substrate

The direct chromogenic assay utilized the substrate methylsulfonyl-D-cyclohexyltyrosyl-glycyl-arginine-p-nitroaniline (Spectrozyme t-PA, American Diagnostica) and was performed as previously described (Strandberg, L., and Madison, E. L. (1995) J. Biol. Chem. 270, 23444–23449; Smith, J. W., Tachias, K., and Madison, E. L. (1995) J. Biol. Chem. 270, 30486–30490).

Measurement of Second Order Rate Constants for Inhibition by PAI-1

Second order rate constants for the inhibition of wild type human t-PA and variant t-PA were measured under pseudo-first order conditions as previously described. Briefly, enzyme and inhibitor were preincubated at 23 degrees Celsius for periods of time varying from 0–30 minutes. Following preincubation, the mixtures were diluted, and the residual enzymatic activity was measured in a standard indirect chromogenic assay. For each enzyme, the concentrations of enzyme and inhibitor and the times of preincubation were chosen to yield several data points for which the residual enzymatic activity varied between 20% and 80% of the initial activity. Data were analyzed by plotting the natural logarithm of the ratio (residual activity/initial activity) versus time of preincubation and measuring the resulting slopes. Division of this slope by -[I] yielded the second order rate constants shown.

It was found that replacement of histidine 417 of t-PA with an acidic residue selectively suppresses the catalytic activity of single chain t-PA. Histidine 417 was replaced by either an aspartate or glutamate residue to yield two variants: t-PA/H417D and t-PA/H417E. Accurate measurement of the enzymatic activity toward plasminogen of the single chain form of these two variants proved difficult, however, because the plasmin produced in this assay rapidly converted the single chain enzymes into their mature, two-chain form by cleaving the R275-I276 peptide bond. Consequently, to overcome this technical difficulty, we also constructed noncleavable forms of the two mutated enzymes by introducing the additional mutation R275E into the existing mutants.

Wild type human t-PA, t-PA/R275E, and all four variants containing mutations at position 417 were expressed by transient expression of COS-1 cells. Since this procedure yielded predominantly single chain enzymes, two-chain t-PAs were generated by treating the enzyme preparations with plasmin-Sepharose (Strandberg, L., and Madison, E. L. (1995) *J. Biol. Chem.* 270, 23444–23449). Quantitative conversion of the enzymes into their mature, two-chain form was confirmed by SDS-PAGE. As expected, variants containing the mutation R275E were synthesized and secreted exclusively as single chain enzymes and were not cleaved by plasmin-Sepharose.

The enzymatic activity of the single and two-chain forms of wild type human t-PA and each variant toward a small synthetic substrate is listed in Table I below. Mutation of histidine 417 had only very modest effects on the activity of the two-chain enzymes. Two-chain t-PA/H417D and t-PA/H417E displayed 67% or 80%, respectively, the activity of the two-chain, wild type human t-PA enzyme in this assay. The H417D and H417E mutations, however, had more significant effects on the activities of the single chain enzymes. Compared to single chain t-PA/R275E, single chain t-PA/R275E,H417D (SEQ ID NO: 1) and t-PA/R275E, H417E (SEQ ID NO: 2) exhibited approximately 16% or 25%, respectively, the activity of single chain t-PA/R275E.

TABLE 1

Kinetic constants for cleavage of the chromogenic substrate Spectrozyme t-PA by single- and two-chain t-PA variants

| Enzyme | $K_{cat}(s^{-1})$ | $K_m$(mM) | $K_{cat}/K_m(M^{-1}s^{-1})$ |
|---|---|---|---|
| Two-chain form | | | |
| t-PA | 59 | 0.4 | $1.5 \times 10^5$ |
| t-PA/H417D | 41 | 0.4 | $1.0 \times 10^5$ |
| t-PA/H417E | 58 | 0.5 | $1.2 \times 10^5$ |
| Single-chain form | | | |
| t-PA/R275E | 26 | 0.7 | $3.7 \times 10^4$ |
| t-PA/R275E,H417D | 5.9 | 1.0 | $5.9 \times 10^3$ |
| t-PA/R275E,H417E | 12 | 1.3 | $9.2 \times 10^3$ |

All of the variants analyzed maintained high enzymatic activity towards the natural substrate, plasminogen, in the presence of the co-factor fibrin (Table II below). The catalytic activity of the two-chain form of wild type human t-PA, t-PA/H417D, and t-PA/H417E varied by a factor of only 1.4. Similarly, the activities of single chain t-PA/R275E, t-PA/R275E,H417D, and t-PA/R275E,H417E differed by a factor of less than 1.8.

TABLE II

Kinetic constants for activation of plasminogen by single- and two-chain t-PA variants in the presence of fibrin

| Enzyme | $K_{cat}(s^{-1})$ | $K_m(\mu M)$ | $K_{cat}/K_m(M^{-1}s^{-1})$ |
|---|---|---|---|
| Two-chain form | | | |
| t-PA | 0.11 | 0.017 | $6.5 \times 10^6$ |
| t-PA/H417D | 0.11 | 0.024 | $4.6 \times 10^6$ |
| t-PA/H417E | 0.10 | 0.022 | $4.5 \times 10^6$ |
| Single-chain form | | | |
| t-PA/R275E | 0.16 | 0.017 | $9.4 \times 10^6$ |
| t-PA/R275E,H417D | 0.23 | 0.043 | $5.3 \times 10^6$ |
| t-PA/R275E,H417E | 0.17 | 0.028 | $6.1 \times 10^6$ |

In the absence of a co-factor, the mutations at position 417 had little effect on the activity of two-chain t-PA toward plasminogen; however, these mutations significantly reduced the catalytic efficiency of single chain t-PA (Table III below). Compared to that of single chain t-PA/R275E, the activity of t-PA/R275E,H417D and t-PA/R275E,H417E was reduced by a factor of approximately 14 or 6, respectively. In this assay, the "zymogenicity", or ratio of the activities of the two-chain and single chain form of a particular enzyme, were approximately 9 for wild type t-PA. By contrast, for variants containing the H417D or H417E mutation, this ratio increased to approximately 150 or 50, respectively (Table III).

TABLE III

Kinetic constants for activation of plasminogen by single- and two-chain variants of t-PA in the absence of a cofactor

| Enzyme | $K_{cat}(s^{-1})$ | $K_m(\mu M)$ | $K_{cat}/K_m(M^{-1}s^{-1})$ |
|---|---|---|---|
| Two-chain form | | | |
| t-PA | 0.093 | 6.7 | $1.4 \times 10^4$ |
| t-PA/H417D | 0.110 | 6.8 | $1.6 \times 10^4$ |
| t-PA/H417E | 0.099 | 8.7 | $1.1 \times 10^4$ |
| Single-chain form | | | |
| t-PA/R275E | 0.014 | 9.5 | $1.5 \times 10^3$ |
| t-PA/R275E,H417D | 0.001 | 9.4 | $1.1 \times 10^2$ |
| t-PA/R275E,H417E | 0.002 | 8.5 | $2.4 \times 10^2$ |

Molecular details of the stimulation of t-PA by fibrin, a complex process that almost certainly involves multiple points of contact between the two proteins, remain unclear. While fibrin stimulation of two-chain t-PA may occur through a single mechanism; stimulation of single chain t-PA by fibrin co-factors, however, appears to utilize at least two distinct mechanisms. First, fibrin apparently stimulates both single- and two-chain t-PA through a templating mechanism resulting in formation of a ternary complex which greatly augments the local concentration of enzyme and substrate. Second, because single- and two-chain t-Pa have equivalent activity in the presence but not the absence of fibrin, it seems likely that binding to fibrin induces a conformational change in the activation domain of single chain t-PA. Similar activation of plasminogen upon binding to streptokinase as well as activation of prothrombin by binding to staphylocoagulase have been described previously. Although the mechanism of this nonclassical, nonproteolytic activation of serine protease zymogens remains completely unclear, the behavior of single chain t-PA/R275E,H417D and t-PA/R275E,H417E indicates that His 417 does not play an essential role in this process. In addition, the properties of two-chain t-PA/H417D and t-PA/H417E indicate that His 417 does not play an essential role during zymogen activation of t-PA through the classical, proteolytic mechanism.

The primary effect of the H417D and H417E mutations was a selective reduction of the activity of single chain t-PA in the absence of fibrin and, consequently, an increase in the zymogenicity of the enzyme. At the molecular level this effect could be mediated either by stabilizing a less active, new conformation of single chain t-PA or by shifting the equilibrium between one or more existing conformations, with distinct activities, towards the less active conformation. Without being held to a single hypothesis, based on structural studies of trypsinogen, trypsin, chymotrypsinogen, and chymotrypsin, that the existence of an equilibrium among multiple conformations of the activation domain is likely to be a general feature of chymotrypsinogen family zymogens.

It is believed that the effect produced by converting His 417 to an acidic residue is mediated by disrupting the important salt bridge between Asp 477 and Lys 429 by providing an alternative, electrostatic interaction for Lys 429. The observation of an electrostatic interaction between K429 and E417 in the recently reported structure of the protease domain of two-chain u-PA, although the distance and geometry of this interaction vary somewhat in the two members of the unit cell in this study, lends credence to this hypothesis. Moreover, as observed in this study, formation of a new salt bridge between Lys 429 and Asp/Glu 417 would be expected to selectively suppress the activity of single chain t-PA because Lys 429 does not interact with Asp 477 in the two-chain enzyme. Instead, in two-chain t-PA, as in other mature chymotrypsin like enzymes, the mature amino terminus inserts into the activation pocket and plays this role. Consequently, as observed, two-chain t-PA/H417D and t-PA/H417E are expected to maintain high catalytic activity. Variants of t-PA containing an acidic residue at position 417, therefore, exhibit significantly enhanced zymogenicity.

TABLE IV

Stimulatory effect of fibrin on the catalytic efficiencies for variants of t-PA

| Enzyme | Fold stimulation of $k_{cat}/K_m$ |
|---|---|
| Two-Chain form | |
| t-PA | 460 |
| t-PA/H417D | 290 |
| t-PA/H417E | 410 |
| Single-chain form | |
| t-PA/R275E | 6300 |
| t-PA/R275E,H417D | 48,200 |
| t-PA/R275E,H417E | 25,400 |

The extent of fibrin stimulation displayed by the single chain form of the mutated enzymes examined in this study is significantly greater than that displayed by wild type t-PA. Wild type, two-chain t-PA possesses a fibrin stimulation factor, defined as the ratio of the catalytic efficiencies in the presence and absence of fibrin, of approximately 460 (Table IV above). The two-chain variants display similar stimulation factors of 290 (t-PA/H417D) and 410 (t-PA/H417E). Single chain wild type t-PA, with a fibrin stimulation factor of 6300, is stimulated to a substantially greater degree than the two-chain enzymes, presumable reflecting the ability of fibrin to stimulate the single chain enzymes not only through a templating mechanism but also by inducing nonproteolytic zymogen activation. Stimulation of single chain t-PA is further enhanced by the H417D or H417E mutations. The fibrin stimulation factors for single chain t-PA/R275E, H417D and t-PA/H417E are 48,200 and 25,400, respectively (Table IV above). Enhanced fibrin stimulation of the variants did not result from increased activity in the presence of fibrin but rather from decreased activity in the absence of a stimulator, an observation consistent with the belief that the effects of these mutations are mediated by disruption of a salt bridge between Lys 429 and Asp 477 in single chain t-PA.

The single chain form of a zymogen-like variant of t-PA is expected to exhibit reduced activity not only towards substrates (Tables I and III, above) but also towards specific inhibitors. To demonstrate this, we measured the second order rate constant for inhibition of single chain t-PA/R275E, t-PA/R275E,H417D, and t-PA/R275E,H417E by the serpin plasminogen activator inhibitor, type 1 (PAI-1) (Table V below). As expected, both variants containing mutations at position 417 exhibited resistance to inhibition by PAI-1. The second order rate constant for inhibition by PAI-1 of t-PA/R275E,H417D or t-PA/R275E,H417E was reduced by factors of approximately 12 or 9, respectively, compared with t-PA/R275E.

TABLE V

Inhibition of wild type and variants of t-PA by PAI-1

| Enzyme | Second Order Rate Constant ($M^{-1}s^{-1}$) |
|---|---|
| t-PA/R275E | $1.8 \times 10^6$ |
| t-PA/R275E,H417D | $1.5 \times 10^5$ |
| t-PA/R275E,H417E | $2.1 \times 10^5$ | t-PA exhibits unusually high catalytic activity as a single chain enzyme and consequently very low zymogenicity. By contrast, a closely related enzyme urokinase (u-PA) exhibits much lower catalytic activity as a single chain enzyme and substantially higher zymogenicity. An important finding of this study is that the presence or absence of a favorable electrostatic interaction between residues at positions 417 and 429 appears to be the major determinant of this key functional distinction between the two human plasminogen activators. The zymogenicity of wild type t-PA, u-PA, and t-PA containing an aspartate at position 417 are approximately 9, 250, and 150, respectively.

These studies demonstrated structure/function relationships within the activation domain of t-PA, and elucidated the molecular basis of important functional distinctions between t-PA and u-PA. These results can also aid the design of improved thrombolytic agents. For example t-PA/R275E, H417D, exhibits substantially enhanced fibrin stimulation, resistance to inhibition by PAI-1, and significantly increased zymogenicity, a useful combination of properties that enhances the therapeutic utility of the enzyme.

EXAMPLE 2

Site Directed Mutagenesis and Construction of Expression Vectors Encoding Variants of t-PA Oligonucleotide directed site specific mutagenesis was performed as described in Example 1. The K429Y mutation was introduced into the 290 bp SacI—SmaI fragment of cDNA encoding t-PA that had been previously subcloned into bacteriophage M13mp18. The mutagenic primer had the following nucleotide sequence:

5'-CGGAGCGGCTGTATGAGGCTCATGT-3' (SEQ ID NO: 10).

Following mutagenesis, ssDNA corresponding to the entire 290 bp SacI—SmaI fragment was fully sequenced to assure the presence of the desired mutation and the absence of any additional mutations. The sequence corresponding to the 290 bp SacI—SmaI fragment of the K429Y mutation is shown in SEQ ID NO: 7. Replicative form (RF) DNA was prepared for appropriate phage, and the mutated 290 bp SacI—SmaI fragment was recovered after digestion of RF DNA with SacI and SmaI and electrophoresis of the digestion products on an agarose gel. The isolated, mutated SacI—SmaI fragment was used to replace the corresponding fragment in full length cDNAs encoding wild type t-PA or t-PA/R275E to yield new, full length cDNAs encoding t-PA/K429Y and t-PA/R275E,K429Y.

Expression of Enzymes by Transient Transfection of COS Cells cDNAs encoding t-PA, t-PA/R275E, t-PA/K429Y, and t-PA/R275E,K429Y were ligated into the transient expression vector pSVT7 and then introduced into COS cells by electroporation using a Bio Rad Gene pulser as described in Example 1. Following electroporation, cells were incubated overnight at 37 degrees Celsius in DMEM containing 10% fetal calf serum and 5mM sodium butyrate. Cells were then washed with serum free medium and incubated in DMEM for 48 hours at 37 degrees Celsius. After the incubation with serum free media, conditioned media were collected and enzyme concentrations were determined by ELISA.

Purification of Wild Type and Mutated Variants of t-PA

Wild type and mutated variants of t-PA were purified using an FPLC system and a 1 ml HiTrap chelating column (Pharmacia Biotech). The column was charged with 0.1 M $CuSO_4$ solution, washed with 5–10 ml distilled water, and equilibrated with start buffer (0.02 M $NaHPO_4$, pH 7.2, 1 M NaCl and 1 mM Imidizole). Conditioned medium containing wild type or variants of t-PA was adjusted to 1 M NaCl and injected into the column with a 50 ml superloop (Pharmacia Biotech). The column was then washed with 10 column volumes of start buffer and eluted using a 0–0.32 M linear gradient of imidizole in the same buffer. Peak fractions were collected and pooled. Purified t-PA samples were concentrated, and buffer was exchanged to 25 mM Tris (pH=7.5), 50 mM NaCl, 1 mM EDTA, using a Centriplus 30 concentrator (Amicon).

Kinetic Analysis of t-PA Activity Using a Small, Synthetic Substrate

The direct chromogenic assay utilized the substrate methylsulfonyl-D-cyclohexyltyrosyl-glycyl-arginine-p-nitroaniline (Spectrozyme t-PA, American Diagnostica) and was performed as described in Example 1.

Kinetic Analysis of Plasminogen Activation Using Indirect Chromogenic Assays

Indirect chromogenic assays of t-PA utilized the substrates lys-plasminogen (American Diagnostica) and Spectrozyme PL (American Diagnostica) and were performed as previously described in Example 1. Assays were performed both in the presence and absence of the co-factor DESAFIB (American Diagnostica).

Indirect Chromogenic Assays in the Presence of Various Fibrin Co-factors

Standard indirect chromogenic assays were performed. Briefly, 0.25–1 ng of enzyme, 0.2 μM lys-plasminogen and 0.62 mM Spectrozyme PL were present in a total volume of 100 μl. Assays were performed either in the presence of buffer, 25 μg/ml DESAFIB, 100 μg/ml fibrinogen, 100 μg/ml cyanogen bromide fragments of fibrinogen (American Diagnostica), or 100 μg/ml of the stimulatory, thirteen amino acid peptide P368. P368 was kindly provided by Marshall Runge (University of Texas Medical Center, Galveston, Tex.). Assays were performed in microtiter plates, and the optical density at 405 nm was measured every 30 seconds for one hour in a Molecular Devices Thermomax. Reactions were performed at 37 degrees Celsius.

Measurement of Second Order Rate Constants for Inhibition by PAI-1

Second order rate constants for the inhibition of wild type and mutated t-PA were measured under pseudo-first order conditions as described in Example 1.

Oligonucleotide directed site specific mutagenesis was used to produce a mutation of Lys 429 of t-PA that selectively suppressed the catalytic activity of single chain t-PA. Lysine 429 was replaced by a tyrosine residue to yield t-PA/K429Y. In addition, to permit accurate measurement of the enzymatic activity toward plasminogen of the single chain form of this variant, a noncleavable form of the mutated enzyme was constructed by introducing the additional mutation R275E into the existing mutant to yield the R275E,K429Y variant.

Wild type t-PA, t-PA/R275E, t-PA/K429Y, and t-PA/R275E,K429Y were expressed by transient expression in COS 1 cells as described in Example 1. Since this procedure yielded predominantly single chain enzymes, two-chain t-PAs were generated by treating the enzyme preparations with plasmin-Sepharose. Quantitative conversion of the enzymes into their mature, two-chain form was confirmed by SDS-PAGE. As previously demonstrated, variants containing the mutation R275E were synthesized and secreted exclusively as single chain enzymes and were not cleaved by plasmin-Sepharose.

TABLE VI

Kinetic constants for cleavage of the chromogenic substrate Spectrozyme t-PA by single- and two-chain t-PA variants

| Enzyme | $K_{cat}(s^{-1})$ | $K_m(mM)$ | $K_{cat}/K_m(M^{-1}s^{-1})$ |
|---|---|---|---|
| Two-chain form | | | |
| t-PA | 40 | 0.5 | $8.0 \times 10^4$ |
| t-PA/K429Y | 35 | 0.5 | $7.0 \times 10^4$ |
| Single-chain form | | | |
| t-PA/R275E | 24 | 0.7 | $3.4 \times 10^4$ |
| t-PA/R275E,K429Y | 0.3 | 0.5 | $6.0 \times 10^2$ |

The enzymatic activity of the single and two-chain forms of wild type and t-PAs toward a small synthetic substrate is listed in Table VI above. Mutation of lysine 429 had little effect on the activity of two-chain t-PA. Two-chain t-PA/K429Y displayed approximately 90% of the activity of the two-chain, wild type enzyme in this assay. By contrast, the K429Y mutation had a very substantial effect on the activity of single chain t-PA. Single chain t-PA/R275E,K429Y exhibited approximately 2% of the activity of single chain t-PA/R275E. In this assay, the zymogenicity, defined as the ratio of the activities of the two-chain to that of the single chain form of a particular enzyme, was approximately 2.5 for wild type t-PA. By contrast, for variants containing the K429Y mutation, this ratio increased to approximately 117 (Table VI).

In the absence of a co-factor, the K429Y mutation had little effect on the activity of two-chain t-PA toward plasminogen; however, this mutation significantly reduced the catalytic efficiency of single chain t-PA (Table VII below). Compared with that of single chain t-PA/R275E, the activity of single chain t-PA/R275E,K429Y was reduced by a factor of 17. By contrast, the activities of two-chain t-PA and t-PA/K429Y differed by a factor of only 1.2.

TABLE VII

Kinetic constants for activation of plasminogen by single- and two-chain variants of t-PA in the absence of a cofactor

| Enzyme | $K_{cat}(s^{-1})$ | $K_m(\mu M)$ | $K_{cat}/K_m(M^{-1}s^{-1})$ |
|---|---|---|---|
| Two-chain form | | | |
| t-PA | 0.16 | 10 | $1.6 \times 10^4$ |
| t-PA/K429Y | 0.18 | 14 | $1.3 \times 10^4$ |
| Single-chain form | | | |
| t-PA/R275E | [0.038] | [30] | $1.3 \times 10^3$ |
| t-PA/R275E,K429Y | 0.00046 | 5.9 | $7.8 \times 10^1$ |

All of the variants analyzed in this study maintained reasonably high enzymatic activity towards the natural substrate plasminogen in the presence of the co-factor fibrin (Table VIII below). The single chain form of variants containing the K429Y mutation were, however, affected to a slightly greater extent than the corresponding mature, two-chain enzymes. Two-chain t-PA/K429Y possessed approximately 75% of the activity of two-chain t-PA while single chain t-PA/R275E,K429Y exhibited approximately 40% of the activity of single chain t-PA/R275E.

TABLE VIII

Kinetic constants for activation of plasminogen by single- and two-chain t-PA variants in the presence of fibrin

| Enzyme | $K_{cat}(s^{-1})$ | $K_m(\mu M)$ | $K_{cat}/K_m(M^{-1}s^{-1})$ |
|---|---|---|---|
| Two-chain form | | | |
| t-PA | 0.08 | 0.02 | $4.0 \times 10^6$ |
| t-PA/K429Y | 0.08 | 0.03 | $3.0 \times 10^6$ |
| Single-chain form | | | |
| t-PA/R275E | 0.10 | 0.02 | $5.0 \times 10^6$ |
| t-PA/R275E,K429Y | 0.10 | 0.07 | $2.0 \times 10^6$ |

The extent of fibrin stimulation displayed by the single chain form of t-PA/R275E,K429Y is significantly greater than that displayed by wild type t-PA. Wild type, two-chain t-PA possesses a fibrin stimulation factor, defined as the ratio of the catalytic efficiencies in the presence and absence of fibrin, of approximately 250 (Table IX below). The two-chain t-PA/K429Y variant displays a similar stimulation factor of 230. Single chain wild type t-PA, with a fibrin stimulation factor of 3800, is stimulated to a substantially greater degree than the two-chain enzymes, presumable reflecting the ability of fibrin to stimulate the single chain enzymes not only through a templating mechanism but also by inducing nonproteolytic zymogen activation. Stimulation of single chain t-Pa is further enhanced by the K429Y mutation. The fibrin stimulation factor for single chain t-PA/R275E,K429Y is approximately 26,000. Enhanced fibrin stimulation of the variant did not result from increased activity in the presence of fibrin but rather from decreased activity in the absence of a stimulator, an observation consistent with our proposal that the effects of these mutations are mediated by disruption of a salt bridge between Lys 429 and Asp 477 in single chain t-PA.

TABLE IX

Stimulatory effect of fibrin on the catalytic efficiencies for variants of t-PA

| Enzyme | Fold stimulation of $k_{cat}/K_m$ |
|---|---|
| Two-chain form | |
| t-PA | 250 |
| t-PA/K429Y | 230 |
| Single-chain form | |
| t-PA/R275E | 3800 |
| t-PA/R275E,K429Y | 26,000 |

The mutated enzyme t-PA/R275E,K429Y is not only stimulated to a significantly greater extent by soluble fibrin than t-PA (Table IX above), but it is also substantially more discriminating among fibrin co-factors than the wild type enzyme (FIG. 2). The two-chain form of both wild type t-PA and t-PA/K429Y are strongly stimulated by soluble fibrin monomers (DESAFIB), fibrinogen, CNBr fragments of fibrinogen, and a 13 amino acid peptide (P368). Single chain t-PA/R275E, on the other hand, is stimulated strongly by soluble fibrin and fibrinogen and moderately by the CNBr fragments and peptide P368. In striking contrast to these enzymes, single chain t-PA/R275E,K429Y, although dramatically stimulated by fibrin monomers, is virtually non-responsive to fibrinogen, CNBr fragments of fibrinogen, peptide P368.

The ratio of the specific activity of a plasminogen activator in the presence of fibrin to that in the presence of fibrinogen, or "fibrin selectivity factor", is one indication of the "clot selectivity" an enzyme will demonstrate in vivo. An enzyme with enhanced fibrin selectivity can accomplish efficient thrombolysis while displaying decreased systemic activity. Under the conditions of the assays reported here, the fibrin selectivity is 1.5 for two-chain t-PA, 1.5 for two-chain t-PA/K429Y, and 1.0 for single chain t-PA/R275E. The fibrin selectivity factor for single chain t-PAIR275E,K429Y, however, is 146. This double mutant, therefore, is approximately two orders of magnitude more discriminating between fibrin and fibrinogen than either single or two-chain wild type t-PA.

The single chain form of a zymogen-like variant of t-PA is expected to exhibit reduced activity not only towards substrates (Tables VI and VIII above) but also towards specific inhibitors. The second order rate constant for inhibition of the single chain form of both t-PA/R275E and t-PA/R275E,K429Y by the serpin plasminogen activator inhibitor, type 1 (PAI-1), the primary physiological inhibitor of t-PA is shown in Table X below. As expected, t-PA/R275E,K429Y exhibited resistance to inhibition by PAI-1. The second order compared with t-PA/R275E.

TABLE X

Inhibition of wild type and variants of t-PA by PAI-1

| Enzyme | Second order rate constant ($M^{-1}s^{-1}$) |
|---|---|
| t-PA/R275E | $1.8 \times 10^6$ |
| t-PA/R275E,K429Y | $7.7 \times 10^3$ |

An important finding of this study is that conversion of lysine 429 to tyrosine residue selectively suppresses the activity of single chain t-PA and thereby substantially enhances the zymogenicity of the enzyme. We have demonstrated, in addition, that single chain t-PA/R275E, K429Y is significantly more fibrin stimulated and substantially more fibrin selective than either single or two-chain, wild type t-PA. Single chain t-PA/R275E,K429Y also exhibits marked resistance to inhibition by PAI-1. It is believed that the effects of this mutation are mediated by disruption of a critical salt bridge formed by Lys 429 and Asp 477 that has been predicted to be present in single- but not two-chain t-PA. The primary role of this putative salt bridge is believed to be stabilization of the active conformation of single chain t-PA. Two-chain t-PA/K429Y, therefor, as demonstrated in this study, is expected to maintain high enzymatic activity.

These results aid in the design of improved thrombolytic agents. For Example t-PA/R275E,K429Y, exhibits significantly enhanced fibrin stimulation, dramatically increased discrimination among fibrin co-factors, marked resistance to inhibition by PAI-1, and substantially increased zymogenicity, a combination of properties that enhance the therapeutic utility of the enzyme.

The foregoing is intended to be illustrative of the present invention, but not limiting. Numerous variations and modifications of the present invention may be effected without departing from the true spirit and scope of the invention.

---

I claim:

1. A variant single chain human tissue-type plasminogen activator protein (SEQ ID NO:1) having R275 and at least one other basic amino acid residue in the serine protease region substituted by a non-basic amino acid residue thereby disrupting the salt bridge interaction between aspartate 477 and lysine 429.

2. The protein of claim 1 wherein the non-basic amino acid residue is chosen from the group consisting of glycine, serine, threonine, asparagine, tyrosine, glutamine, aspartic acid, and glutamic acid and having a zymogenicity of at least 10.

3. The protein of claim 1 having a zymogenicity of at least 75.

4. The protein of claim 1 having a zymogenicity of at last 100.

5. The protein of claim 1 having a fibrin stimulation factor of at least 10,000.

6. The protein of claim 1 having a fibrin stimulation factor of at least 20,000.

7. The protein of claim 2 having a fibrin stimulation factor of at least 10,000.

8. The protein of claim 2 having a fibrin stimulation factor of at least 20,000.

9. The protein of claim 3 having a fibrin stimulation factor of at least 20,000.

10. The protein of claim 1 wherein the protein is at least a factor of 5 less inhibited by PAI-1 compared to wild type single chain human tissue-type plasminogen activator protein.

11. The protein of claim 1 wherein the protein is at least a factor of 9 less inhibited by PAI-1 compared to wild type single chain human tissue-type plasminogen activator protein.

12. The protein of claim 1 wherein the protein is at least a factor of 200 less inhibited by PAI-1 compared to wild type single chain human tissue-type plasminogen activator protein.

13. The protein of claim 8 wherein the protein is at least a factor of 9 less inhibited by PAI-1 compared to wild type single chain human tissue-type plasminogen activator protein.

14. The protein of claim 8 wherein the protein is at least a factor of 200 less inhibited by PAI-1 compared to wild type single chain human tissue-type plasminogen activator protein.

15. The protein of claim 1 wherein the protein has a fibrin selectivity factor of at least 100.

16. The protein of claim 8 wherein the protein has a fibrin selectivity factor of at least 100.

17. The protein of claim 14 wherein the protein has a fibrin selectivity factor of at least 100.

18. A variant single chain human tissue-type plasminogen activator protein, selected from the group consisting of R275E,H417D, R275E,H417E and R275E,K429Y.

19. A composition for the treatment of an thrombotic condition comprising a physiologically effective amount of the protein of claim 1 in a pharmaceutically suitable excipient.

20. The composition or claim 19 wherein the dose of the protein is from about 0.05 milligram per kilogram body weight to about 0.2 milligrams per kilogram body weight.

21. A diagnostic kit comprising the protein (SEQ ID NO:1) of claim 1.

22. A variant single chain human tissue-type plasminogen activator protein (SEQ ID NO:1) with the amino acid substitutions R275E and K429Y.

* * * * *

SEQUENCE LISTING

<160> NUMBER OF SEQ ID NOS: 10

<210> SEQ ID NO 1
<211> LENGTH: 527
<212> TYPE: PRT
<213> ORGANISM: Homo sapiens

<400> SEQUENCE: 1

```
Ser Tyr Gln Val Ile Cys Arg Asp Glu Lys Thr Gln Met Ile Tyr Gln
 1               5                  10                  15

Gln His Gln Ser Trp Leu Arg Pro Val Leu Arg Ser Asn Arg Val Glu
            20                  25                  30

Tyr Cys Trp Cys Asn Ser Gly Arg Ala Gln Cys His Ser Val Pro Val
        35                  40                  45

Lys Ser Cys Ser Glu Pro Arg Cys Phe Asn Gly Gly Thr Cys Gln Gln
    50                  55                  60

Ala Leu Tyr Phe Ser Asp Phe Val Cys Gln Cys Pro Glu Gly Phe Ala
65                  70                  75                  80

Gly Lys Cys Cys Glu Ile Asp Thr Arg Ala Thr Cys Tyr Glu Asp Gln
                85                  90                  95

Gly Ile Ser Tyr Arg Gly Thr Trp Ser Thr Ala Glu Ser Gly Ala Glu
            100                 105                 110

Cys Thr Asn Trp Asn Ser Ser Ala Leu Ala Gln Lys Pro Tyr Ser Gly
        115                 120                 125

Arg Arg Pro Asp Ala Ile Arg Leu Gly Leu Gly Asn His Asn Tyr Cys
    130                 135                 140

Arg Asn Pro Asp Arg Asp Ser Lys Pro Trp Cys Tyr Val Phe Lys Ala
145                 150                 155                 160

Gly Lys Tyr Ser Ser Glu Phe Cys Ser Thr Pro Ala Cys Ser Glu Gly
                165                 170                 175

Asn Ser Asp Cys Tyr Phe Gly Asn Gly Ser Ala Tyr Arg Gly Thr His
            180                 185                 190

Ser Leu Thr Glu Ser Gly Ala Ser Cys Leu Pro Trp Asn Ser Met Ile
        195                 200                 205

Leu Ile Gly Lys Val Tyr Thr Ala Gln Asn Pro Ser Ala Gln Ala Leu
    210                 215                 220

Gly Leu Gly Lys His Asn Tyr Cys Arg Asn Pro Asp Gly Asp Ala Lys
```

```
225              230              235              240

Pro Trp Cys His Val Leu Lys Asn Arg Arg Leu Thr Trp Glu Tyr Cys
                245                  250                  255

Asp Val Pro Ser Cys Ser Thr Cys Gly Leu Arg Gln Tyr Ser Gln Pro
                260                  265                  270

Gln Phe Glu Ile Lys Gly Gly Leu Phe Ala Asp Ile Ala Ser His Pro
                275                  280                  285

Trp Gln Ala Ala Ile Phe Ala Lys His Arg Arg Ser Pro Gly Glu Arg
                290                  295                  300

Phe Leu Cys Gly Gly Ile Leu Ile Ser Ser Cys Trp Ile Leu Ser Ala
305                  310                  315                  320

Ala His Cys Phe Gln Glu Arg Phe Pro Pro His His Leu Thr Val Ile
                325                  330                  335

Leu Gly Arg Thr Tyr Arg Val Val Pro Gly Glu Glu Glu Gln Lys Phe
                340                  345                  350

Glu Val Glu Lys Tyr Ile Val His Lys Glu Phe Asp Asp Asp Thr Tyr
                355                  360                  365

Asp Asn Asp Ile Ala Leu Leu Gln Leu Lys Ser Asp Ser Ser Arg Cys
                370                  375                  380

Ala Gln Glu Ser Ser Val Val Arg Thr Val Cys Leu Pro Pro Ala Asp
385                  390                  395                  400

Leu Gln Leu Pro Asp Trp Thr Glu Cys Glu Leu Ser Gly Tyr Gly Lys
                405                  410                  415

Asp Glu Ala Leu Ser Pro Phe Tyr Ser Glu Arg Leu Lys Glu Ala His
                420                  425                  430

Val Arg Leu Tyr Pro Ser Ser Arg Cys Thr Ser Gln His Leu Leu Asn
                435                  440                  445

Arg Thr Val Thr Asp Asn Met Leu Cys Ala Gly Asp Thr Arg Ser Gly
                450                  455                  460

Gly Pro Gln Ala Asn Leu His Asp Ala Cys Gln Gly Asp Ser Gly Gly
465                  470                  475                  480

Pro Leu Val Cys Leu Asn Asp Gly Arg Met Thr Leu Val Gly Ile Ile
                485                  490                  495

Ser Trp Gly Leu Gly Cys Gly Gln Lys Asp Val Pro Gly Val Tyr Thr
                500                  505                  510

Lys Val Thr Asn Tyr Leu Asp Trp Ile Arg Asp Asn Met Arg Pro
                515                  520                  525

<210> SEQ ID NO 2
<211> LENGTH: 527
<212> TYPE: PRT
<213> ORGANISM: Homo sapiens

<400> SEQUENCE: 2

Ser Tyr Gln Val Ile Cys Arg Asp Glu Lys Thr Gln Met Ile Tyr Gln
1                5                   10                  15

Gln His Gln Ser Trp Leu Arg Pro Val Leu Arg Ser Asn Arg Val Glu
                20                  25                  30

Tyr Cys Trp Cys Asn Ser Gly Arg Ala Gln Cys His Ser Val Pro Val
                35                  40                  45

Lys Ser Cys Ser Glu Pro Arg Cys Phe Asn Gly Gly Thr Cys Gln Gln
                50                  55                  60

Ala Leu Tyr Phe Ser Asp Phe Val Cys Gln Cys Pro Glu Gly Phe Ala
65                  70                  75                  80
```

-continued

```
Gly Lys Cys Cys Glu Ile Asp Thr Arg Ala Thr Cys Tyr Glu Asp Gln
                85                  90                  95
Gly Ile Ser Tyr Arg Gly Thr Trp Ser Thr Ala Glu Ser Gly Ala Glu
            100                 105                 110
Cys Thr Asn Trp Asn Ser Ser Ala Leu Ala Gln Lys Pro Tyr Ser Gly
        115                 120                 125
Arg Arg Pro Asp Ala Ile Arg Leu Gly Leu Gly Asn His Asn Tyr Cys
    130                 135                 140
Arg Asn Pro Asp Arg Asp Ser Lys Pro Trp Cys Tyr Val Phe Lys Ala
145                 150                 155                 160
Gly Lys Tyr Ser Ser Glu Phe Cys Ser Thr Pro Ala Cys Ser Glu Gly
                165                 170                 175
Asn Ser Asp Cys Tyr Phe Gly Asn Gly Ser Ala Tyr Arg Gly Thr His
            180                 185                 190
Ser Leu Thr Glu Ser Gly Ala Ser Cys Leu Pro Trp Asn Ser Met Ile
        195                 200                 205
Leu Ile Gly Lys Val Tyr Thr Ala Gln Asn Pro Ser Ala Gln Ala Leu
    210                 215                 220
Gly Leu Gly Lys His Asn Tyr Cys Arg Asn Pro Asp Gly Asp Ala Lys
225                 230                 235                 240
Pro Trp Cys His Val Leu Lys Asn Arg Arg Leu Thr Trp Glu Tyr Cys
                245                 250                 255
Asp Val Pro Ser Cys Ser Thr Cys Gly Leu Arg Gln Tyr Ser Gln Pro
            260                 265                 270
Gln Phe Glu Ile Lys Gly Gly Leu Phe Ala Asp Ile Ala Ser His Pro
        275                 280                 285
Trp Gln Ala Ala Ile Phe Ala Lys His Arg Arg Ser Pro Gly Glu Arg
    290                 295                 300
Phe Leu Cys Gly Gly Ile Leu Ile Ser Ser Cys Trp Ile Leu Ser Ala
305                 310                 315                 320
Ala His Cys Phe Gln Glu Arg Phe Pro Pro His His Leu Thr Val Ile
                325                 330                 335
Leu Gly Arg Thr Tyr Arg Val Val Pro Gly Glu Glu Glu Gln Lys Phe
            340                 345                 350
Glu Val Glu Lys Tyr Ile Val His Lys Glu Phe Asp Asp Asp Thr Tyr
        355                 360                 365
Asp Asn Asp Ile Ala Leu Leu Gln Leu Lys Ser Asp Ser Ser Arg Cys
    370                 375                 380
Ala Gln Glu Ser Ser Val Val Arg Thr Val Cys Leu Pro Pro Ala Asp
385                 390                 395                 400
Leu Gln Leu Pro Asp Trp Thr Glu Cys Glu Leu Ser Gly Tyr Gly Lys
                405                 410                 415
Glu Glu Ala Leu Ser Pro Phe Tyr Ser Glu Arg Leu Lys Glu Ala His
            420                 425                 430
Val Arg Leu Tyr Pro Ser Ser Arg Cys Thr Ser Gln His Leu Leu Asn
        435                 440                 445
Arg Thr Val Thr Asp Asn Met Leu Cys Ala Gly Asp Thr Arg Ser Gly
    450                 455                 460
Gly Pro Gln Ala Asn Leu His Asp Ala Cys Gln Gly Asp Ser Gly Gly
465                 470                 475                 480
Pro Leu Val Cys Leu Asn Asp Gly Arg Met Thr Leu Val Gly Ile Ile
                485                 490                 495
Ser Trp Gly Leu Gly Cys Gly Gln Lys Asp Val Pro Gly Val Tyr Thr
```

```
                    500             505             510
Lys Val Thr Asn Tyr Leu Asp Trp Ile Arg Asp Asn Met Arg Pro
                515             520             525

<210> SEQ ID NO 3
<211> LENGTH: 527
<212> TYPE: PRT
<213> ORGANISM: Homo sapiens

<400> SEQUENCE: 3

Ser Tyr Gln Val Ile Cys Arg Asp Glu Lys Thr Gln Met Ile Tyr Gln
 1               5                  10                  15

Gln His Gln Ser Trp Leu Arg Pro Val Leu Arg Ser Asn Arg Val Glu
            20                  25                  30

Tyr Cys Trp Cys Asn Ser Gly Arg Ala Gln Cys His Ser Val Pro Val
        35                  40                  45

Lys Ser Cys Ser Glu Pro Arg Cys Phe Asn Gly Thr Cys Gln Gln
     50                  55                  60

Ala Leu Tyr Phe Ser Asp Phe Val Cys Gln Cys Pro Glu Gly Phe Ala
 65                  70                  75                  80

Gly Lys Cys Cys Glu Ile Asp Thr Arg Ala Thr Cys Tyr Glu Asp Gln
                 85                  90                  95

Gly Ile Ser Tyr Arg Gly Thr Trp Ser Thr Ala Glu Ser Gly Ala Glu
            100                 105                 110

Cys Thr Asn Trp Asn Ser Ser Ala Leu Ala Gln Lys Pro Tyr Ser Gly
        115                 120                 125

Arg Arg Pro Asp Ala Ile Arg Leu Gly Leu Gly Asn His Asn Tyr Cys
130                 135                 140

Arg Asn Pro Asp Arg Asp Ser Lys Pro Trp Cys Tyr Val Phe Lys Ala
145                 150                 155                 160

Gly Lys Tyr Ser Ser Glu Phe Cys Ser Thr Pro Ala Cys Ser Glu Gly
                165                 170                 175

Asn Ser Asp Cys Tyr Phe Gly Asn Gly Ser Ala Tyr Arg Gly Thr His
            180                 185                 190

Ser Leu Thr Glu Ser Gly Ala Ser Cys Leu Pro Trp Asn Ser Met Ile
        195                 200                 205

Leu Ile Gly Lys Val Tyr Thr Ala Gln Asn Pro Ser Ala Gln Ala Leu
210                 215                 220

Gly Leu Gly Lys His Asn Tyr Cys Arg Asn Pro Asp Gly Asp Ala Lys
225                 230                 235                 240

Pro Trp Cys His Val Leu Lys Asn Arg Arg Leu Thr Trp Glu Tyr Cys
                245                 250                 255

Asp Val Pro Ser Cys Ser Thr Cys Gly Leu Arg Gln Tyr Ser Gln Pro
            260                 265                 270

Gln Phe Glu Ile Lys Gly Gly Leu Phe Ala Asp Ile Ala Ser His Pro
        275                 280                 285

Trp Gln Ala Ala Ile Phe Ala Lys His Arg Arg Ser Pro Gly Glu Arg
    290                 295                 300

Phe Leu Cys Gly Gly Ile Leu Ile Ser Ser Cys Trp Ile Leu Ser Ala
305                 310                 315                 320

Ala His Cys Phe Gln Glu Arg Phe Pro Pro His His Leu Thr Val Ile
                325                 330                 335

Leu Gly Arg Thr Tyr Arg Val Val Pro Gly Glu Glu Gln Lys Phe
            340                 345                 350
```

```
Glu Val Glu Lys Tyr Ile Val His Lys Glu Phe Asp Asp Asp Thr Tyr
            355                 360                 365

Asp Asn Asp Ile Ala Leu Leu Gln Leu Lys Ser Asp Ser Ser Arg Cys
        370                 375                 380

Ala Gln Glu Ser Ser Val Val Arg Thr Val Cys Leu Pro Pro Ala Asp
385                 390                 395                 400

Leu Gln Leu Pro Asp Trp Thr Cys Glu Leu Ser Gly Tyr Gly Lys
                405                 410                 415

His Glu Ala Leu Ser Pro Phe Tyr Ser Glu Arg Leu Tyr Glu Ala His
            420                 425                 430

Val Arg Leu Tyr Pro Ser Ser Arg Cys Thr Ser Gln His Leu Leu Asn
            435                 440                 445

Arg Thr Val Thr Asp Asn Met Leu Cys Ala Gly Asp Thr Arg Ser Gly
        450                 455                 460

Gly Pro Gln Ala Asn Leu His Asp Ala Cys Gln Gly Asp Ser Gly Gly
465                 470                 475                 480

Pro Leu Val Cys Leu Asn Asp Gly Arg Met Thr Leu Val Gly Ile Ile
                485                 490                 495

Ser Trp Gly Leu Gly Cys Gly Gln Lys Asp Val Pro Gly Val Tyr Thr
            500                 505                 510

Lys Val Thr Asn Tyr Leu Asp Trp Ile Arg Asp Asn Met Arg Pro
            515                 520                 525

<210> SEQ ID NO 4
<211> LENGTH: 290
<212> TYPE: DNA
<213> ORGANISM: Homo sapiens

<400> SEQUENCE: 4
ctacggcaag catgaggcct tgtctccttt ctattcggag cggctgaagg aggctcatgt     60
cagactgtac ccatccagcc gctgcacatc acaacattta cttaacagaa cagtcaccga    120
caacatgctg tgtgctggag acactcggag cggcgggccc caggcaaact tgcacgacgc    180
ctgccagggc gattcgggag ccccctggt gtgtctgaac gatggccgca tgactttggt    240
gggcatcatc agctggggcc tgggctgtgg acagaaggat gtcccgggtg               290

<210> SEQ ID NO 5
<211> LENGTH: 290
<212> TYPE: DNA
<213> ORGANISM: Homo sapiens

<400> SEQUENCE: 5
ctacggcaag gacgaggcct tgtctccttt ctattcggag cggctgaagg aggctcatgt     60
cagactgtac ccatccagcc gctgcacatc acaacattta cttaacagaa cagtcaccga    120
caacatgctg tgtgctggag acactcggag cggcgggccc caggcaaact tgcacgacgc    180
ctgccagggc gattcgggag ccccctggt gtgtctgaac gatggccgca tgactttggt    240
gggcatcatc agctggggcc tgggctgtgg acagaaggat gtcccgggtg               290

<210> SEQ ID NO 6
<211> LENGTH: 290
<212> TYPE: DNA
<213> ORGANISM: Homo sapiens

<400> SEQUENCE: 6
ctacggcaag gaggaggcct tgtctccttt ctattcggag cggctgaagg aggctcatgt     60
```

-continued

```
cagactgtac ccatccagcc gctgcacatc acaacattta cttaacagaa cagtcaccga    120
caacatgctg tgtgctggag acactcggag cggcgggccc caggcaaact tgcacgacgc    180
ctgccagggc gattcgggag gcccctggt gtgtctgaac gatggccgca tgactttggt    240
gggcatcatc agctggggcc tgggctgtgg acagaaggat gtcccgggtg              290
```

<210> SEQ ID NO 7
<211> LENGTH: 290
<212> TYPE: DNA
<213> ORGANISM: Homo sapiens

<400> SEQUENCE: 7

```
ctacggcaag catgaggcct tgtctccttt ctattcggag cggctgtatg aggctcatgt     60
cagactgtac ccatccagcc gctgcacatc acaacattta cttaacagaa cagtcaccga    120
caacatgctg tgtgctggag acactcggag cggcgggccc caggcaaact tgcacgacgc    180
ctgccagggc gattcgggag gcccctggt gtgtctgaac gatggccgca tgactttggt    240
gggcatcatc agctggggcc tgggctgtgg acagaaggat gtcccgggtg              290
```

<210> SEQ ID NO 8
<211> LENGTH: 23
<212> TYPE: DNA
<213> ORGANISM: Homo sapiens

<400> SEQUENCE: 8

```
ctacggcaag gacgaggcct tgt                                            23
```

<210> SEQ ID NO 9
<211> LENGTH: 23
<212> TYPE: DNA
<213> ORGANISM: Homo sapiens

<400> SEQUENCE: 9

```
ctacggcaag gaggaggcct tgt                                            23
```

<210> SEQ ID NO 10
<211> LENGTH: 26
<212> TYPE: DNA
<213> ORGANISM: Homo sapiens

<400> SEQUENCE: 10

```
cggagcggct gtatgaggct mcatgt                                         26
```